United States Patent
Salmond et al.

(10) Patent No.: US 6,507,022 B1
(45) Date of Patent: Jan. 14, 2003

(54) OPTICAL APPARATUS

(75) Inventors: Colin Herbert Salmond, Beerwah (AU); Colin Victor Greensill, Rockhampton (AU); Peter Leigh-Jones, Gordon (AU)

(73) Assignee: Elan Group Ltd., Queensland (AU)

( * ) Notice: Subject to any disclaimer, the term of this patent is extended or adjusted under 35 U.S.C. 154(b) by 0 days.

(21) Appl. No.: 09/700,904

(22) PCT Filed: May 21, 1999

(86) PCT No.: PCT/AU99/00387

§ 371 (c)(1),
(2), (4) Date: Nov. 21, 2000

(87) PCT Pub. No.: WO99/61898

PCT Pub. Date: Dec. 2, 1999

(30) Foreign Application Priority Data

May 21, 1998 (AU) .............................................. PP 3652

(51) Int. Cl.[7] .............................................. G01N 21/35
(52) U.S. Cl. ................................................ 250/339.06
(58) Field of Search ....................... 250/339.06, 339.07, 250/339.11, 339.12

(56) References Cited

U.S. PATENT DOCUMENTS

| | | | |
|---|---|---|---|
| 3,910,701 A | * 10/1975 | Henderson et al. | ........... 356/39 |
| 5,077,477 A | 12/1991 | Stroman et al. | ........... 250/349 |
| 5,089,701 A | 2/1992 | Dull et al. | ........... 250/339.08 |
| 5,206,701 A | * 4/1993 | Taylor et al. | ........... 356/325 |
| 5,319,437 A | * 6/1994 | Van Aken et al. | ........... 356/326 |
| 5,394,237 A | * 2/1995 | Chang et al. | ........... 356/328 |
| 5,708,273 A | * 1/1998 | VonBargen | ........... 250/339.11 |
| 5,751,421 A | * 5/1998 | Wright et al. | ........... 356/328 |
| 5,751,424 A | * 5/1998 | Bostater, Jr. | ........... 356/342 |
| 5,937,157 A | * 8/1999 | Oshiyama et al. | ........... 713/200 |

FOREIGN PATENT DOCUMENTS

| | | | | |
|---|---|---|---|---|
| AU | A5504494 | 8/1995 | | |
| EP | 402877 A1 | * 12/1990 | ........... | G01N/33/12 |
| EP | 0758081 A2 | 2/1997 | | |
| EP | 0764844 A2 | 3/1997 | | |

* cited by examiner

*Primary Examiner*—Constantine Hannaher
*Assistant Examiner*—Shun Lee
(74) *Attorney, Agent, or Firm*—Young & Thompson

(57) ABSTRACT

An optical apparatus (10) is provided for non-destructive examination of characteristics of an object (102). The apparatus has a light source (28) for directing a beam of NIR Light towards the object (102), an aperture (24) for diverging the NIR beam through or reflected from the object, a collimating lens (30) for collimating the divergent beam, a diffraction device (32) for separating the collimated beam into wavelength components and focusing lens (36) for focusing the wavelength components onto a matrix of photodetectors (34) which in turn produce electrical output signals proportional to energy levels in the wavelength components. The apparatus (10) can be made compact so that it can be used to examine objects in fields. In one example the apparatus (10) has a pistol-shaped housing with a slot (12) in its turret (18) and a body (16) with a display monitor (14). The body (16) also has an opening through which a correlation device (26) in the form of a PCMCIA card can be connected to the apparatus (1). The apparatus (1) is typically used to examine physiological stages of plants in fields so that the grower can determine the appropriate actions required for acceptable plant growth.

30 Claims, 13 Drawing Sheets

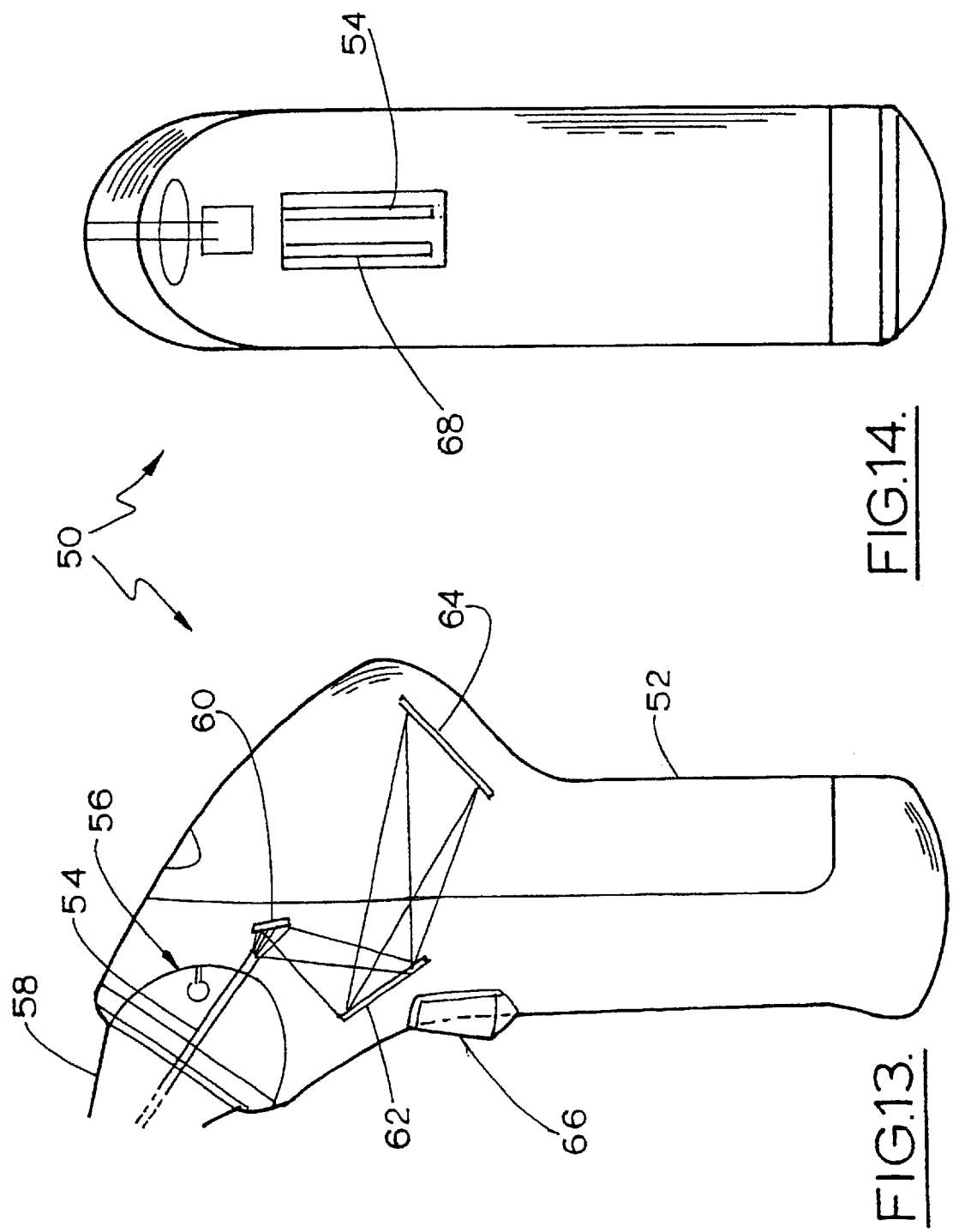

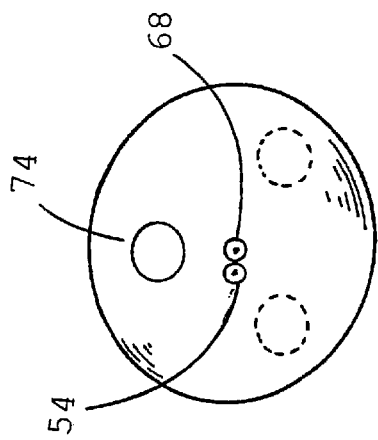
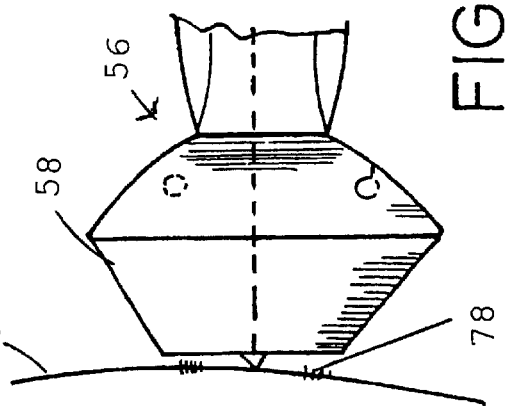
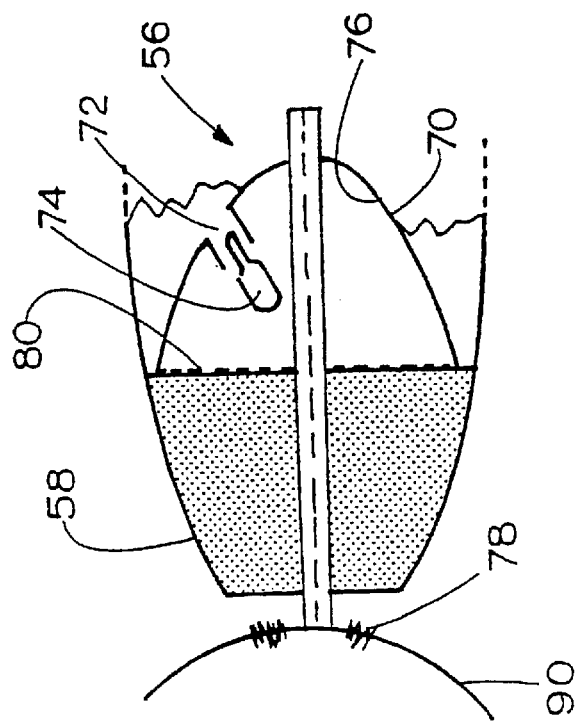

OPTICAL APPARATUS

TECHNICAL FIELD OF THE INVENTION

This invention relates to an optical apparatus for examining an object and in particular but not limited to an optical apparatus for examining carbohydrate constituents in a plant.

BACKGROUND OF THE INVENTION

Current methods for optically examining objects such as strawberries and other plants require obtaining samples of the objects and examining the samples in laboratories. These methods are inconvenient as the apparatuses for examination cannot be used on the objects in situ or in the fields. They are also destructive as samples must be taken off the objects.

The existing optical apparatuses for the examination do not have the resolution nor the sensitivity which are sufficiently high for reliably examining constituents in fruits or plants in general. They also cannot be easily adapted for examining relative concentrations of the constituents.

These apparatuses have a light source arranged to direct light onto an object and a light detector arranged for detecting reflected or scattered light from the object. The detector must be positioned outside the light path of the source and at some distance from the object in order not to interfere with the light from the source.

The detectors of these prior art apparatuses receive light reflected off the surface of and light scattered from within the object, together with reflected and scattered light from other surfaces. The light received by the detectors therefore include a high degree of noise signals.

The prior art apparatuses also require a relatively high powered light source as a large amount of the light from the source do not reach the target regions of the object.

OBJECT OF THE INVENTION

An object of the present invention is to alleviate or to reduce to a certain degree one or more of the prior art disadvantageous.

SUMMARY OF THE INVENTION

In one aspect the present invention resides in an optical apparatus for examining an object. The apparatus comprises a light source adapted to direct a beam of light towards an object under examination, an aperture arranged for receiving the light reflected from, scattered within or passing through the object and, for the beam of light to diverge therefrom means for collimating light arranged so that the beam of light through the aperture incident thereat is collimated. The apparatus also comprises means for dispersing the collimated beam of light from the collimating means into wavelength components, and means for providing electrical output signals which are respectively proportional to energy levels in the wavelength components.

In preference, the apparatus further comprises means for processing the output signals and thereby providing one or more indication signals for respectively indicating one or more characteristics of the object.

An indication means can be arranged for receiving the one or more indication signals and indicating the or each said indication signals in a suitable form. Desirably the indication means is a printer, a display monitor or a combination thereof.

The apparatus may have an interface means to which a computer may be selectively connected thereto for storing the one or more indication signals and/or for further processing the one or more indication signals.

Typically the processing means includes a data correlation device adapted to relate the or each of said indication signals to a characteristic of the object.

The data correlation device may have a set of correlation data for one object or a plurality of sets of correlation data for different types of objects.

Each said characteristic may be any constituent or a relative concentration of any constituent of the object. Examples of the constituents are carbohydrates, starch and sugars including sucrose, glucose, fructose and the like. The characteristic may also relate to any physiological state of the object The physiological states may include growth state, maturity state in plant and the like.

Desirably each said characteristics is a signature of vigour of growth, maturity for picking or any other physiological state of a plant.

Conveniently the data correlation device is removably connectable to the apparatus so that the apparatus can be selectively connected to the data correlation device having a set of correlation data for a particular object under examination.

The data correlation device may conveniently be in the form of a printed circuit card such as a PCMCIA card.

Preferably the output signal providing means includes an detection arrangement for detecting the wavelength components.

It is further preferred that the apparatus has a focusing arrangement for focusing the wavelength components onto the detection arrangement.

The light source may include an illuminator for producing an annulus of light onto the object. The illuminator comprises a hollow body having a reflective interior surface, and one or more lamps disposed so that at least some portions of the light from said one or more lamps are reflected from the reflective surface. The reflective surface is configured so that the light reflected therefrom forms an annulus of light on a region of the object.

In preference said hollow body is substantially conical or half egg shell shaped. The hollow body may also have a substantially parabolic cross section.

Suitably the annulus of light is arranged around a light detection probe for detecting scattered light from said object. The detection probe is suitably positioned along an axis of the hollow body and the light source is positioned at an angle to said axis.

Advantageously the illuminator is provided with a shroud downstream of the light reflected from said reflective surface. In one from the shroud is substantially frusto-conical or curvilinear in shape The shroud may have a partly or wholly reflective interior surface for redirecting portions of the light from said light source and/or said interior surface of the body to said region of the object.

The shroud may have a rear wall arranged to direct light towards the annulus. The rear wall may be curve shaped or formed as a Fresnel lens.

It is desired that the shroud is removably fixed so that it can be easily replaced. The shroud may be configured for a particularly shaped object. The illuminator can therefore be used for different objects by selecting suitable shrouds for the different objects.

It is also preferred that the apparatus comprises an optical conveying means for conveying the beam of light reflected from or through the object to the aperture. The conveying means may include an optical fibre such as a 500 μm diameter optical fibre with a 11° numerical opening. The optical fibre may be arranged within a protective probe.

The aperture can be positioned at about the focal length of the collimating means. It may have one or more parallel slits of a suitable width. In one example the width is 10 μm. Typically the one or more slits are vertically oriented.

Desirably, the position of the collimating means relative to the aperture is adjustable so that the desired resolution and intensity of the apparatus can be easily changed.

Suitably, the collimating means is a collimating lens and typically an achromatic lens.

The dispersing means may include one or more prisms of any suitable configuration. The one or more prisms are preferably equilateral prism(s).

The focusing arrangement may include one or more focusing lenses for focusing the wavelength components onto the detection arrangement. Desirably the one or more focusing lenses are configured so that a linear dispersion of the spectrum can be provided across the detection arrangement. Plano-convex lenses are examples of the focusing lenses.

The detection arrangement preferably includes a plurality of detection elements which provide the electrical output signals in response to detection of the wavelength components.

More preferably the detection elements are arranged in a matrix of at least 2×2 (4) detection elements. Typically the matrix has 32×32 (2048) or 64×64 (4096) detection elements.

The detection arrangement conveniently has a charge coupled device (CCD) and the detection elements are in the form of picture elements (pixels).

The light source may be selected from any suitable known sources. It is preferred that the light source is near infrared radiation (NIR).

Desirably, the apparatus has a housing means in which components of the apparatus are located. The housing means may have a substantially light proof first housing member in which the collimating means, the dispersing means and electrical signal providing means are located. The first housing member reduces or eliminates interference from background radiation and reflections from optical surfaces. More desirably the aperture is also located within the first housing member.

More desirably, the housing means is compact so that the apparatus can be used on field or in situ. Typically the housing means is arranged so that in use a user can hold the apparatus in one hand. Alternatively it can be arranged so that it can be worn on a part of the user body such as on a wrist. The housing means may be shaped like a wrist watch, a hand pistol or any other suitable configuration.

The housing means may have a second housing member in which the light source is located and the second housing member has a gap into which at least part of the object can be inserted. It is advantageous that the second, housing member is removably connectable to the first housing member so that the second housing member can be selected from a plurality of second housing members adapted for examining particular kinds of objects.

Where the apparatus is provided with an optical conveying means the conveying means is preferably located in the second housing member.

The first housing member advantageously has the indication means arranged therein. It is also advantageous that the first housing means has the data correlation device removably connected thereto so that the apparatus can be used for different objects.

In one example, the first housing member is shaped like the body of a hand pistol and the second housing member is shaped like a turret of the pistol.

Said reflective surface of the hollow body may be formed according to a method comprises the steps of:

(a) selecting one portion of the reflective interior surface;

(b) calculating the orientation of said portion which will reflect a ray of light from a light source disposed within the hollow body onto the annulus of light in the same axial plane as said ray of light;

(c) stepping to another portion which is in the same vertical plane as said one portion and repeating step (b);

(d) repeating step (c) until said portions can be joined to form a ring; and (e) repeating steps (a) to (d) for forming another ring adjacent to said ring until the rings extend to a desired area.

Preferably in the step (c) the direction of stepping reverses on completion of half a revolution.

The adjacent portions in each ring may be joined at the intersection of the respective planes containing said adjacent portions, or at about mid way between the intersection and one of said adjacent portions.

BRIEF DESCRIPTION OF THE INVENTION

In order that the present invention can be readily understood and put into practical effect the description will now be made in reference to the accompanying drawings which illustrate non-limiting embodiments of the present invention, and wherein:

FIG. 13 is a side view of a hand gun shaped embodiment of the optical apparatus according to the present invention;

FIG. 14 shows a rear view of the apparatus shown in FIG. 13;

FIG. 15 is a schematic drawing of an embodiment of the illuminator according to the present invention;

FIG. 16 is a schematic drawing of another embodiment of the illuminator according to the present invention;

FIG. 17 is a rear view of the illuminator shown in FIG. 16;

DETAILED DESCRIPTION OF THE INVENTION

Figure 1:
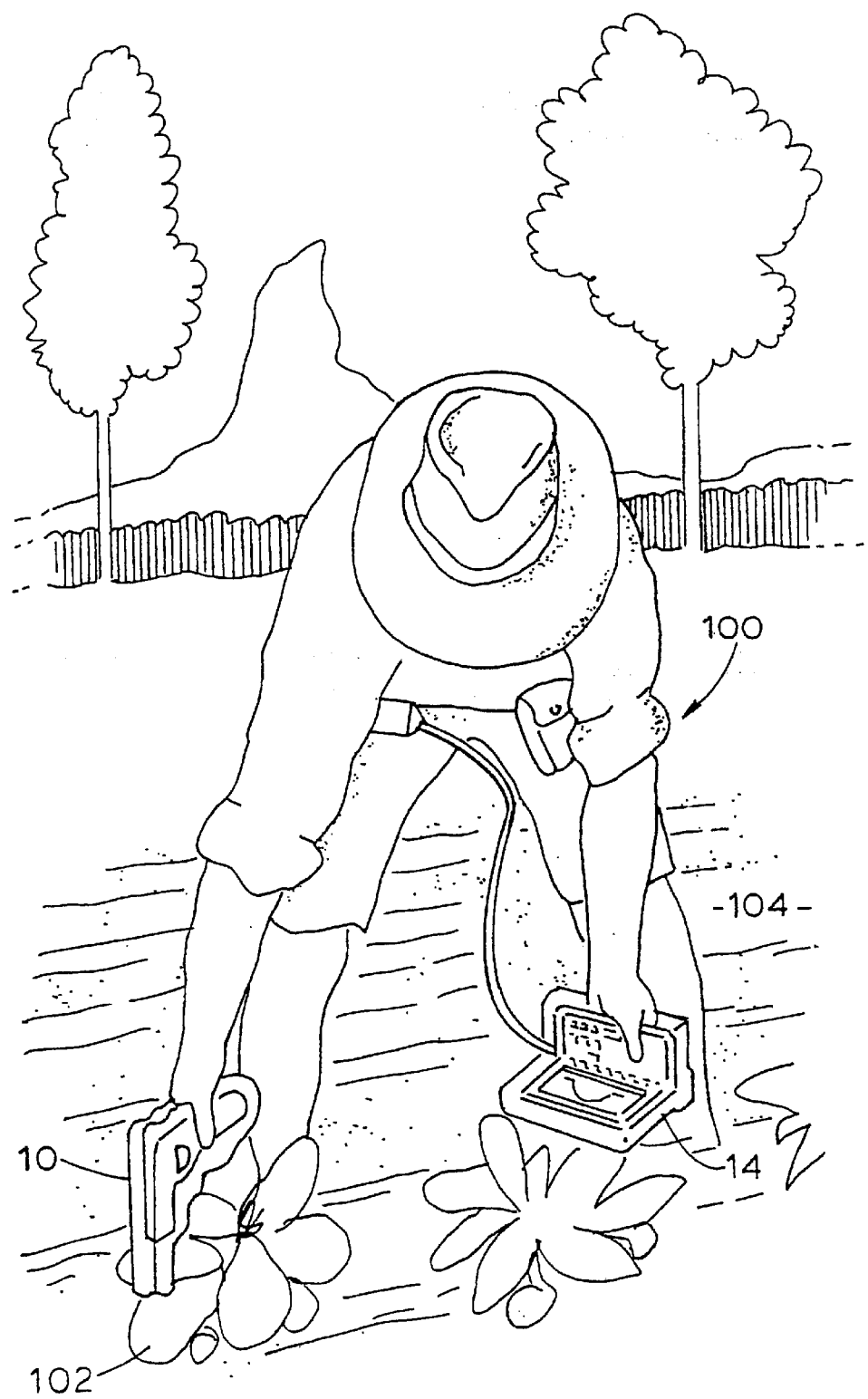
FIG. 1 shows an embodiment of the optical apparatus according to the present invention being used by an operator for examining a strawberry plant in a field.

Referring initially to FIG. 1, there is shown an optical apparatus 10 according to the present invention being used by an operator 100 to examine a characteristic, in this case the state of growth (vigour), of an object 102 (strawberry plant) in a field 104.

The apparatus 10 in this example is pistol-shaped. It has a slot 12 (shown more clearly in FIG. 2) for receiving a leave of the strawberry plant 102 under examination. An indication means 14 exemplified by a palm-top computer is connected to the apparatus 10 for indicating a characteristic spectrum of the strawberry plant 102.

Figure 2:
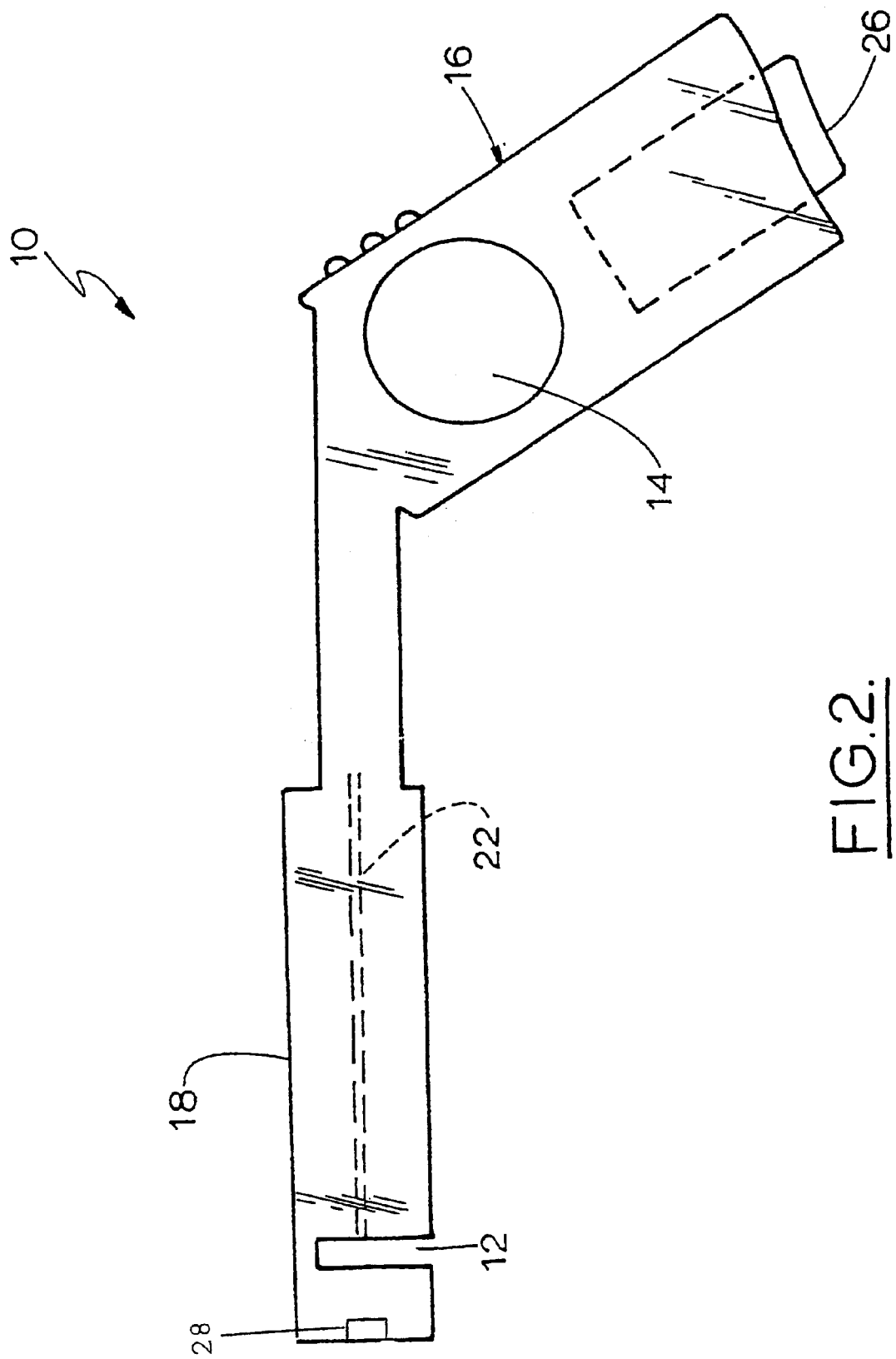
FIG. 2 shows a pistol-shaped embodiment of the optical apparatus according to the present invention.

FIG. 2 is another embodiment of the optical apparatus 10 and in this case the apparatus 10 is in the shape of a pistol. The apparatus 10 has a housing made up of a pistol body shaped first housing member 16 which is substantially light proof and a turret shaped second housing member 18. The second housing member 18 is removably connected to the first housing member 16.

The second housing member 18 has a slot 12 for receiving a part of an object to be examined. On one side of the slot 12 is located a light source 28 (see FIGS. 3 and 4) and on the opposite side is a light conveying means 22 in the form of an optic fibre.

The first housing member 16 has a slit 24 (see FIGS. 3 and 4) positioned to receive light from the optic fibre 22. It also has a removably connectable data correlation device 26 in the form of a PCMCIA card. The card 26 has a memory in which correlation data for one or more varieties of plants are stored. The indication means 14 which in this example is an LCD screen is provided for displaying output signals relating to one or more characteristics of an object under examination.

The removable card 26 can be easily replaced so that the apparatus 10 can be used for a variety of different objects. As an example if the apparatus 10 is to be used for examining sugars in a strawberry plant, a card 26 having correlation data for sugars in strawberry plants is selected and inserted into the first housing member 16.

Figure 3:
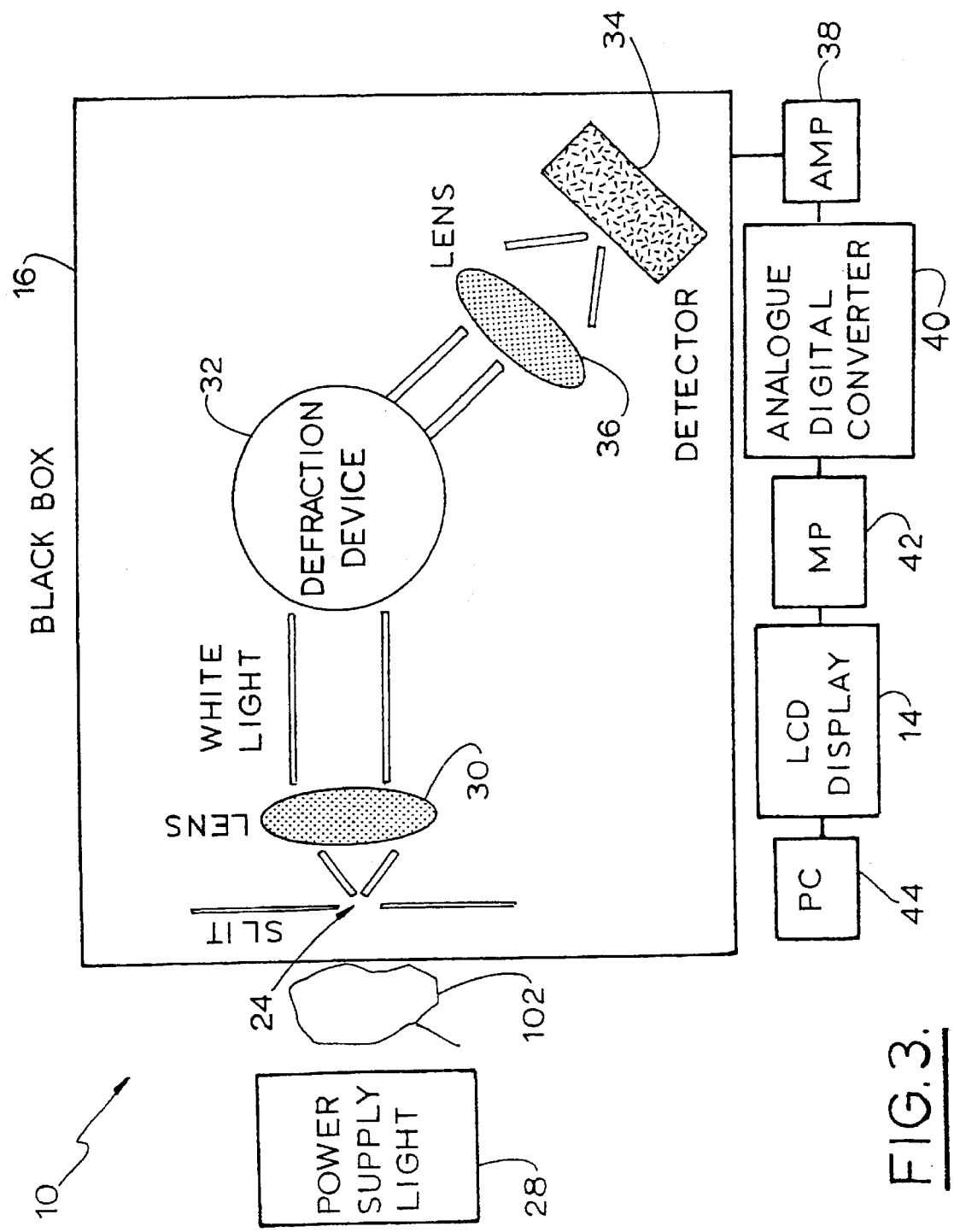
FIG. 3 is a diagrammatic representation of the components of the apparatus according to the present invention.

FIG. 3 shows a diagrammatic representation of the apparatus 10 according to one embodiment of the present invention. In this embodiment the apparatus 10 has a resolution defining slit 24 arranged for receiving a beam of light from a light source 28 and at about the focal length of a collimating lens 30. The beam of light enters the slit 24 and travels divergently onto the collimating lens 30 which collimates the light into a parallel beam of light. A dispersing means 32 in the form of a diffraction device is positioned in the path of the collimated beam. The diffraction device 32 separates the collimated beam into its wavelength components. A detection means 34, in this case a photodetecting device, is positioned downstream of the diffraction device 32 for detecting the wavelength components and to produce electrical output signals proportional to energy levels in the wavelength components.

Focusing means 36 in the form of a focusing lens is positioned between the diffraction device 32 and the detection means 34 so that the discrete component wavelengths are brought to a sharp or focused point on the detection means 34.

A light proof first housing member 16 is used to minimise interference from light reflected from other surfaces.

The electrical output signals from the detection means 34 are then amplified in an amplifier 38 and converted to digital form by an analogue to digital converter 40. A processing means (microprocessor) 42 is arranged for processing the digital signals in accordance with instructions in a suitable program and the data in a data correlation device. The processed signals are displayed on indication means 14 (LCD monitor in this example).

A computer 44 is also connected to the processing means 42 for downloading or further processing the signals.

Figure 4:
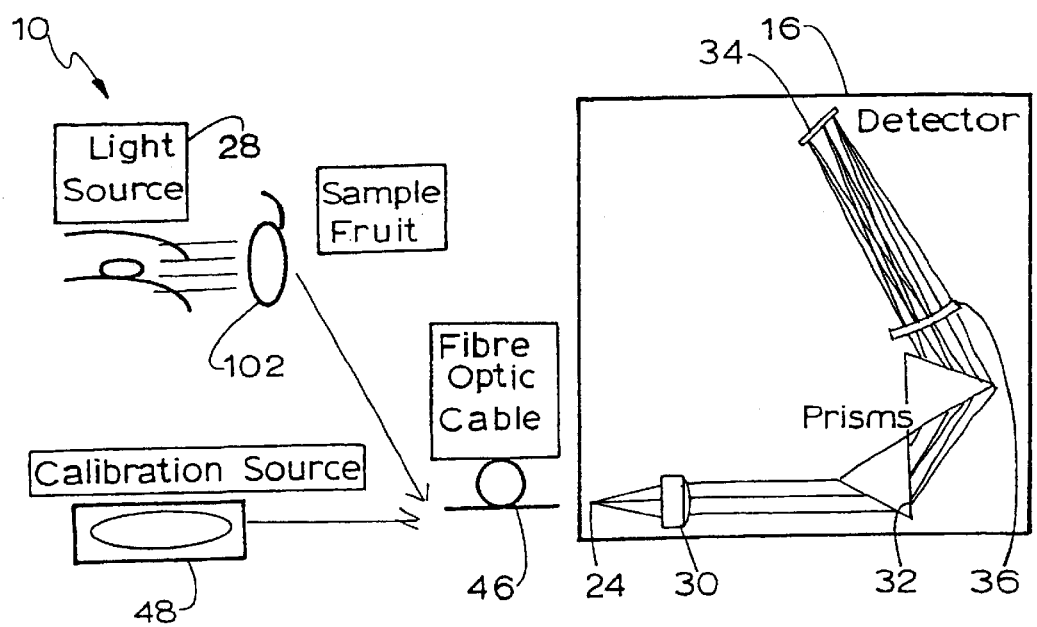
FIG. 4 is another diagrammatic representation of the components of the apparatus according to the present invention.

FIG. 4 shows another embodiment of the apparatus 10. In this embodiment the apparatus 10 has a light conveying means (an optic fibre) 46 for conveying the light through the object 102 to the slit 24. The means 46 is a 500 $\mu$m diameter optic fibre with 11° numerical aperture. The slit 24 is a vertical parallel slit of 10 $\mu$m width and is mounted at about the focal length of the collimating means 30. An achromatic lens is employed as the collimating means 30.

The dispersion means 32 in this case are dual equilateral prisms which provide higher resolution. Two plano-convex lenses are used as the focusing means 36 in order to have a substantially linear dispersion of the spectrum across the detection means 34. In this case, means 34 is a charge coupled device (CCD) having 2048 pixel and a polymer window with pixel dimensions of 14 $\mu$m (h) by 12 $\mu$m (w) on a 14 $\mu$m spacing). Typically integration times for the collection of spectra are in the range of 10–100 ms.

A calibration source 48 such as a commercially available mercury-argon discharge source sold under the name of Ocean Optic HG 1 can be removably coupled to the optic fibre 46 for calibrating the apparatus 10.

The light source 28 in this embodiment is a 90–100 w tungsten halogen bulb powered by a low ripple DC power supply. The bulb is mounted at the primary focus of an elliptically reflector.

The object 102 under examination is positioned at about the secondary focus of the reflector.

Figure 5:
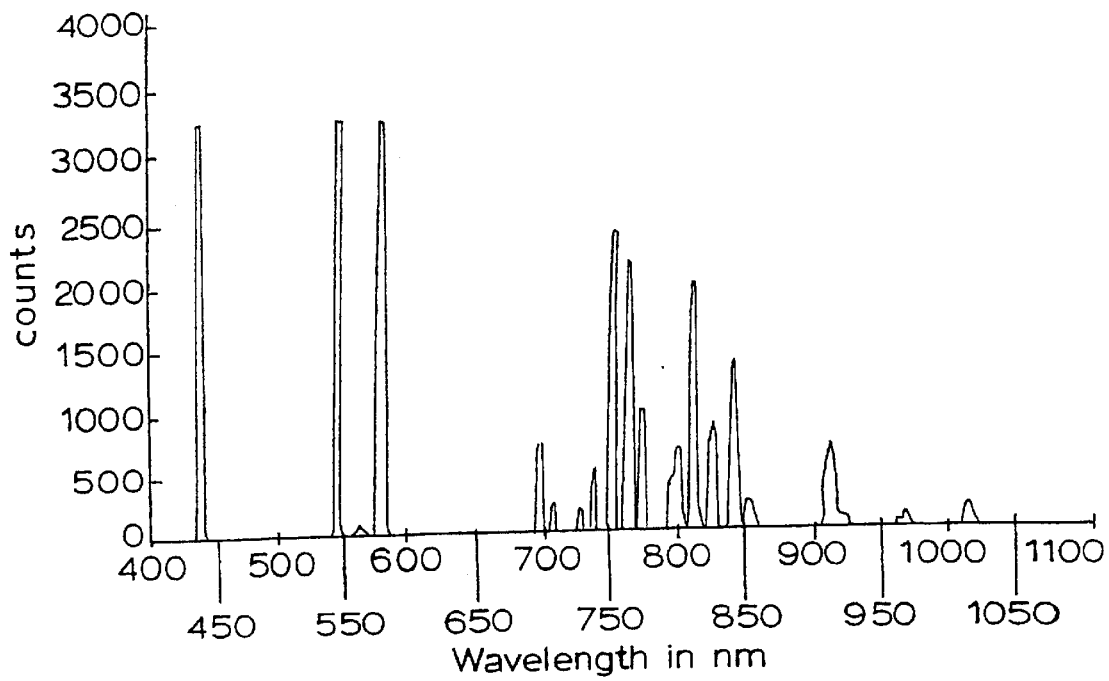
FIG. 5 shows a typical spectrum obtained with the optical apparatus according to the present invention.

In a test the apparatus 10 as shown diagrammatically in FIG. 4 is used to obtain spectrum of a mercury-argon discharge source. The test result is shown in FIG. 5.

Figure 6:
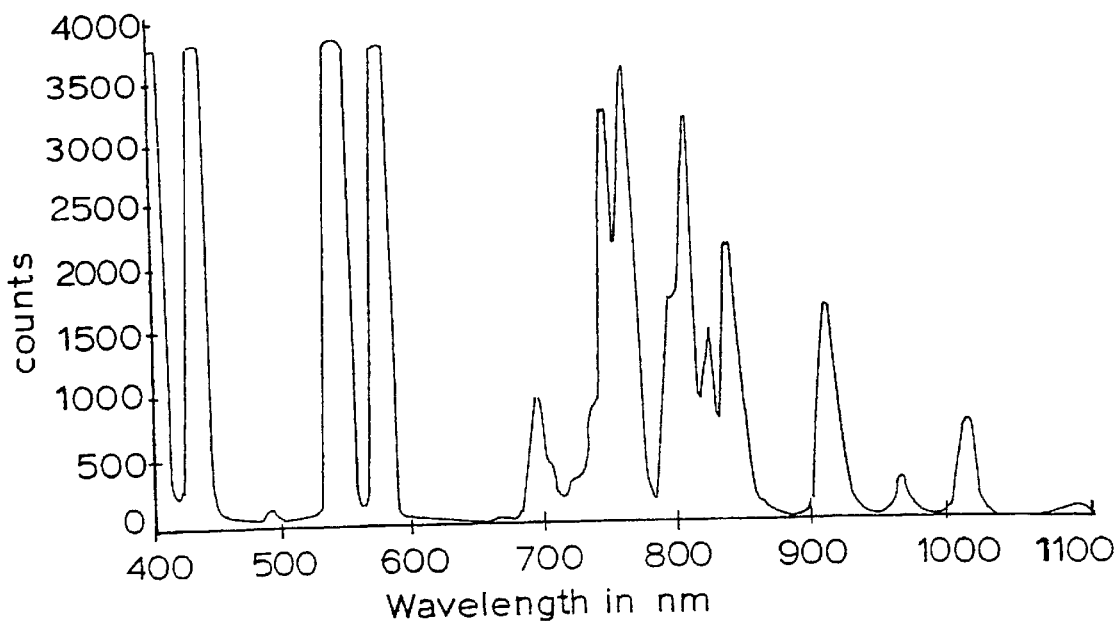
FIG. 6 shows a typical spectrum obtained with a prior art optical apparatus.

The same test is repeated using a commercial prior art spectrometer and the result is shown in FIG. 6.

When the test results are compared it is noted that both the apparatus 10 according to the invention and the prior art spectrometer display a wide useful bandwidth from about 400–1025 nm. But the apparatus 10 demonstrates a superior performance in terms of resolution and sensitivity.

As can be seen the apparatus 10 is about three times more sensitive as spectra of similar intensity were recorded in about 15 ms compared to 50 ms for the prior art. The resolution of the apparatus 10 varies from about 4 nm (FWHM) at a wavelength of 696 nm to about 9 nm (FWHM) across the same band width. FWHM refers to full width at half maximum.

Figure 7:
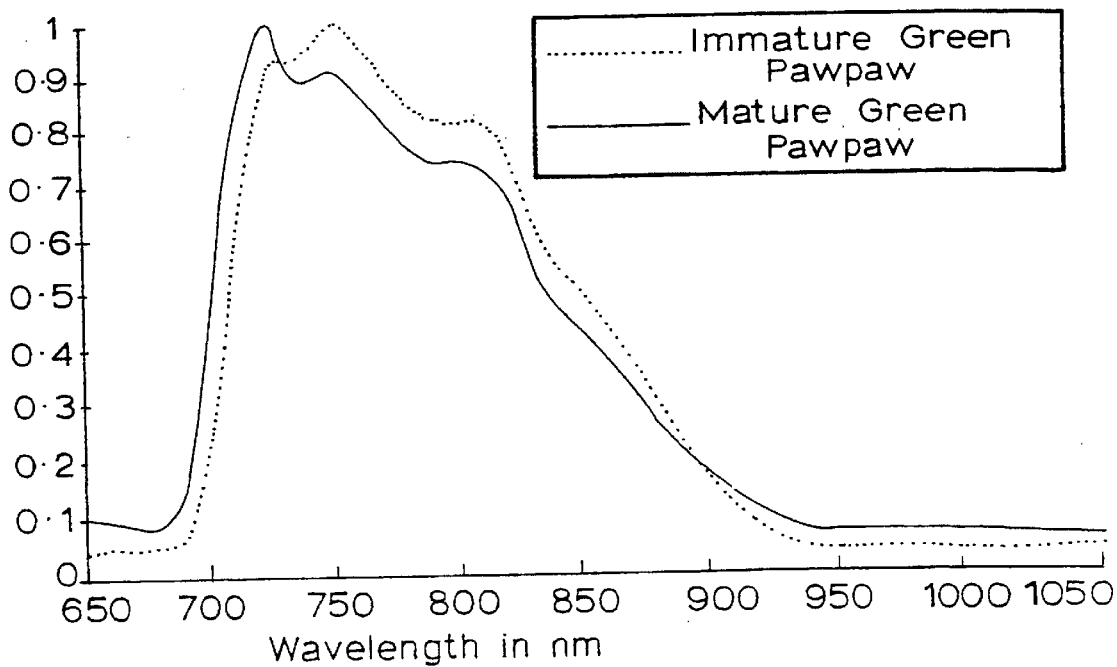
FIG. 7 shows a comparison of the spectra of mature and immature green pawpaw sample obtained with the optical apparatus according to the invention.

The apparatus 10 as shown in FIG. 4 has been used to examine the NIR transmission spectra of various fruits. FIG. 7 shows the respective NIR transmission spectra of 60 mm thick sections of immature and mature green paw paws (Canica papaya). The figure shows a definite shift in the wave length of peak light transmission from 755 mm in the immature sample to 730 in the mature sample.

Thus the apparatus 10 can be used to determined when green pawpaws can be picked as fruits will not continue to ripen to an edible state when picked while in the immature state.

Figure 8:
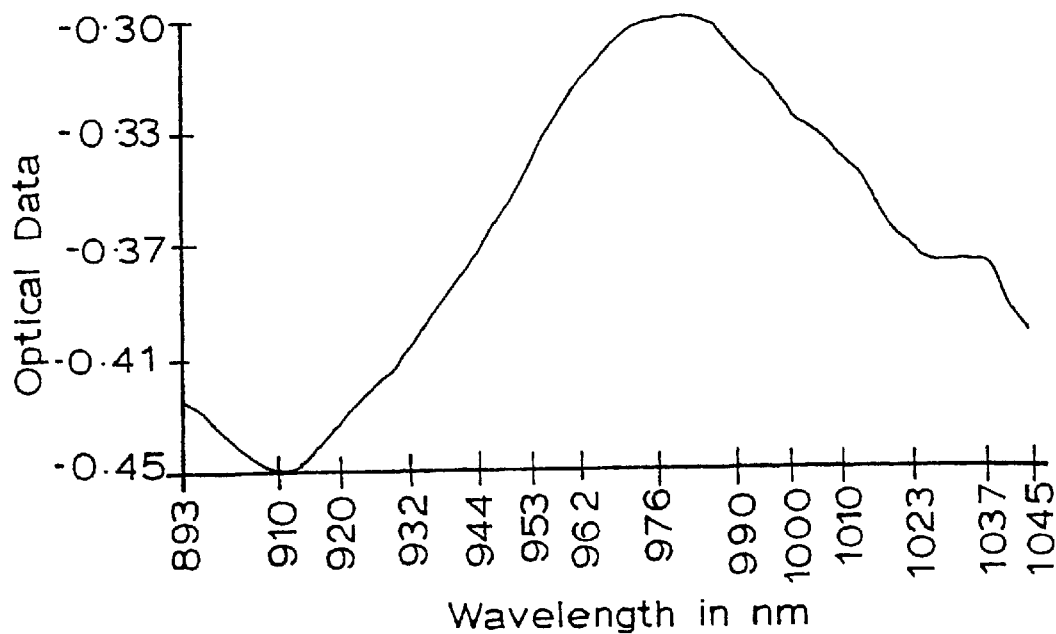
FIG. 8 shows a spectrum of a sample of lychee fruit obtained with the optical apparatus according to the present invention.
Figure 9:
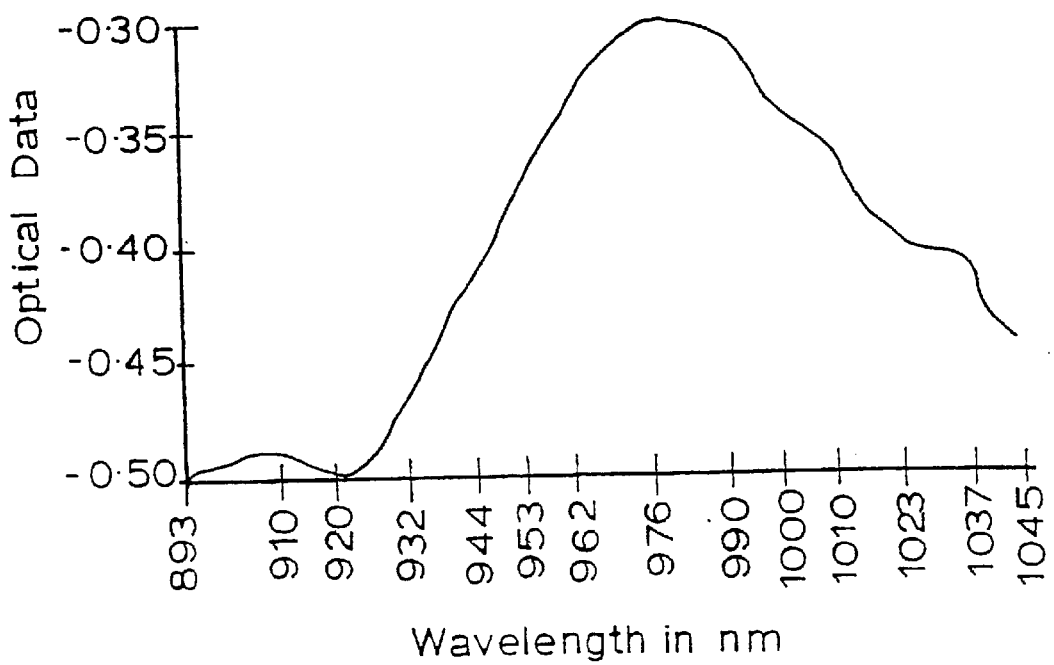
FIG. 9 shows spectrum of another sample of lychees fruit obtained with optical apparatus according to the present invention.

FIGS. 8 and 9 show spectra of two different samples of lychee fruits. The differences between the two spectra can be used to indicate certain characteristic of the samples.

Figure 10:
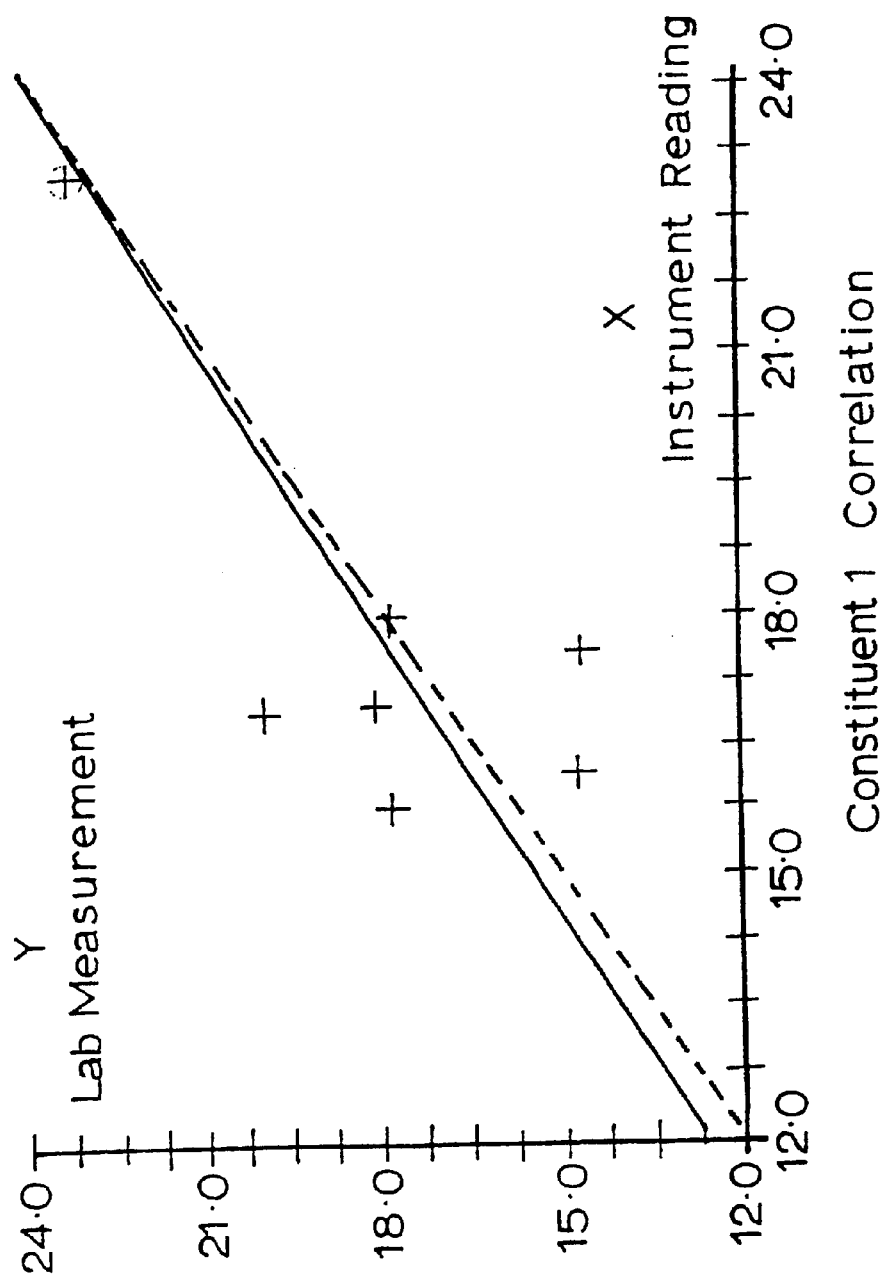
FIGS. 10 to 12 shows graphs of calibration data for constituent sugars in a plant.
Figure 11:
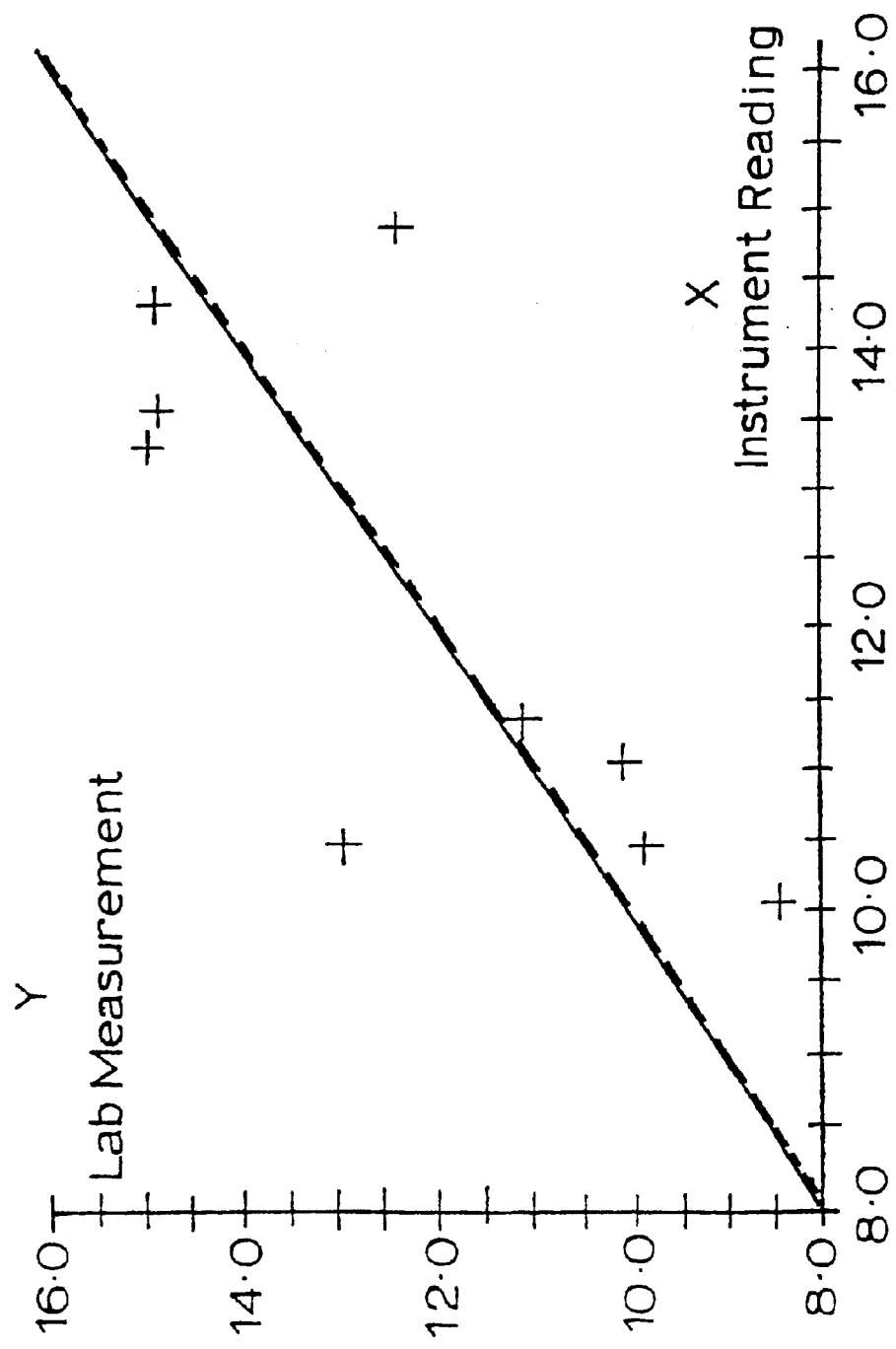
Figure 12:
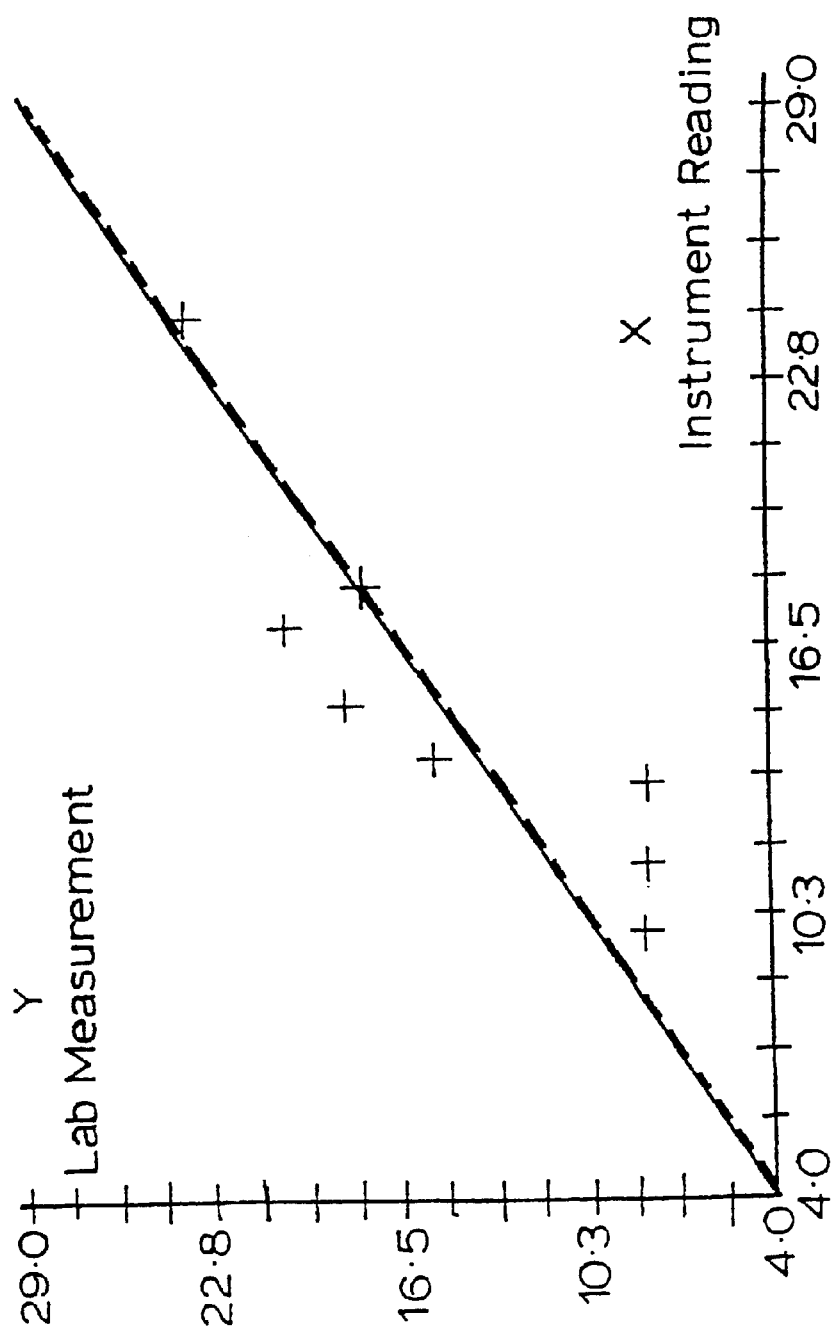

FIGS. 10 to 12 show graphical correlation data of three constituents of the vigour sugars in a fruit for determination by the apparatus 10 The respective slopping dotted and firm lines represent slope and bias corrections. The data obtained for the calibrations of the constituents are as outlined in the following correlation data tables.

Constituent 1 correlation data

| Instrument Reading X | | Lab Measurement Y | | |
|---|---|---|---|---|
| Mean X | 16.709 | Mean Y | 17.042 | B (Slope) | 0.955 |
| Stand Dev X | 2.894 | Stand Dev Y | 3.279 | A (Slope Bias) | 1.079 |
| X min | 12.000 | Y min | 12.240 | Bias (No Slope) | 0.333 |
| X max | 22.840 | Y max | 23.210 | | |

| | | | | |
|---|---|---|---|---|
| RMS | | 1.803 | Correlation Coeff | 0.843 |
| Standard Error (Bias Corrected) | | 1.768 | Coeff of Determination | 0.711 |
| Standard Error (Slope and Bias Corrected) | | 1.885 | | |

| | Lab Measurement Y | Instrument Reading X | Difference Y-X | Predictions Y (e) | Difference Y-Y (e) |
|---|---|---|---|---|---|
| 1 = 37 | 12.24 | 12.00 | 0.24 | 12.54 | −0.30 |
| 2 = 28 | 15.15 | 14.76 | 0.39 | 15.18 | −0.03 |
| 3 = 44 | 17.76 | 15.70 | 2.06 | 16.08 | 1.68 |
| 4 = 41 | 14.68 | 17.50 | −2.82 | 17.80 | −3.12 |
| 5 = 43 | 14.69 | 16.08 | −1.39 | 16.44 | −1.75 |
| 6 = 25 | 19.92 | 16.75 | 3.17 | 17.08 | 2.84 |
| 7 = 19 | 17.66 | 17.88 | −0.22 | 18.16 | −0.50 |
| 8 = 24 | 18.07 | 16.87 | 1.20 | 17.20 | 0.87 |
| 9 = 14 | 23.21 | 22.84 | 0.37 | 22.90 | 0.31 |

Constituent 2 correlation data

| Instrument Reading X | | Lab Measurement Y | | |
|---|---|---|---|---|
| Mean X | 12.109 | Mean Y | 12.109 | B (Slope) | 1.000 |
| Stand Dev X | 1.818 | Stand Dev Y | 2.424 | A (Slope Bias) | −0.004 |
| X min | 10.040 | Y min | 8.420 | Bias (No Slope) | 0.000 |
| X max | 14.770 | Y max | 14.870 | | |

| | | | | |
|---|---|---|---|---|
| RMS | | 1.603 | Correlation Coeff | 0.750 |
| Standard Error (Bias Corrected) | | 1.603 | Coeff of Determination | 0.563 |
| Standard Error (Slope and Bias Corrected) | | 1.714 | | |

| | Lab Measurement Y | Instrument Reading X | Difference Y-X | Predictions Y (e) | Difference Y-Y (e) |
|---|---|---|---|---|---|
| 1 = 37 | 12.33 | 14.77 | −2.44 | 14.77 | −2.44 |
| 2 = 28 | 8.42 | 10.04 | −1.62 | 10.04 | −1.62 |
| 3 = 44 | 14.87 | 13.24 | 1.63 | 13.24 | 1.63 |
| 4 = 41 | 14.80 | 13.49 | 1.31 | 13.49 | 1.31 |
| 5 = 43 | 14.80 | 14.23 | 0.57 | 14.23 | 0.57 |
| 6 = 25 | 11.05 | 11.31 | −0.26 | 11.31 | −0.26 |
| 7 = 19 | 9.81 | 10.44 | −0.63 | 10.44 | −0.63 |
| 8 = 24 | 10.04 | 11.02 | −0.98 | 11.02 | −0.98 |
| 9 = 14 | 12.86 | 10.44 | 2.42 | 10.44 | 2.42 |

Constituent 3 correlation data

| Instrument Reading X | | Lab Measurement Y | | |
|---|---|---|---|---|
| Mean X | 14.021 | Mean Y | 14.020 | B (Slope) | 1.000 |
| Stand Dev X | 5.535 | Stand Dev Y | 6.264 | A (Slope Bias) | 0.001 |
| X min | 4.120 | Y min | 6.810 | Bias (No Slope) | −0.001 |
| X max | 24.000 | Y max | 23.460 | | |

| | | | | |
|---|---|---|---|---|
| RMS | | 2.933 | Correlation Coeff | 0.884 |
| Standard Error (Bias Corrected) | | 2.933 | Coeff of Determination | 0.781 |
| Standard Error (Slope and Bias Corrected) | | 3.135 | | |

| | Lab Measurement Y | Instrument Reading X | Difference Y-X | Predictions Y (e) | Difference Y-Y (e) |
|---|---|---|---|---|---|
| 1 = 37 | 6.81 | 4.12 | 2.69 | 4.12 | 2.69 |
| 2 = 28 | 15.27 | 13.90 | 1.37 | 13.90 | 1.37 |
| 3 = 44 | 8.20 | 11.43 | −3.23 | 11.43 | −3.23 |
| 4 = 41 | 8.16 | 13.19 | −5.03 | 13.19 | −5.03 |
| 5 = 43 | 8.17 | 9.90 | −1.73 | 9.90 | −1.73 |
| 6 = 25 | 20.09 | 16.86 | 3.23 | 16.86 | 3.23 |
| 7 = 19 | 17.80 | 17.77 | 0.03 | 17.77 | 0.03 |
| 8 = 24 | 18.22 | 15.02 | 3.20 | 15.02 | 3.20 |
| 9 = 14 | 23.46 | 24.00 | −0.54 | 24.00 | −0.54 |

The spectrometer instrument used for obtaining correlation data is Zelta ZX100F Near Infrared (NIR) analyser.

For each of the constituents 1 to 3, 9 samples were randomly selected. The sample identifications corresponding to the selected samples are indicated in each case.

The prediction values Y (e) are values after slope and bias corrections.

As can be seen the results are as follows:

| Constituent | Correlation | Standard Error |
|---|---|---|
| 1 | 0.86 | 1.8 |
| 2 | 0.75 | 1.7 |
| 3 | 0.88 | 2.9 |

The correlation data allows identification of the constituents in the sample.

As the constituents of the sample absorb some energy levels but allow other energy levels (or wavelength components) to pass, the apparatus 10 can be used to determined relative concentrations of the constituents by monitoring the energy levels (or wavelength components) which pass through he sample and which do not pass through.

Any mathematical analysis method can be employed. The applicant prefers partial least squares (PLS) regression analysis or minimum message length (MML) single and multiple factor analysis such as described.

Referring initially to FIG. 13, there is shown a near infrared (NIR) optical apparatus 50 according to another embodiment of the present invention. The apparatus 50 in this example has a substantially hand gun shaped casing 52. In the body 52 are arranged a light detection probe 54 positioned at substantially in the center axis of an illuminator 56. The probe 54 extends from just within a frustoconical shaped shroud 58 to immediately before a mirror 60.

As can be seen the light beams detected by the probe 54 are deflected off the mirror 60 onto a diffraction grating 62. The grating 62 directs the beams substantially parallelly onto an array of charge coupled diodes (CCD) or photodiodes 64.

A trigger 66 for activating the apparatus 50 is provided for pressing by a finger of a user.

The components of the apparatus 50 are mounted on a frame (not shown) made of a stable aluminium or titanium based cast or machined alloy for thermal stability and mechanical strength. The frame is mounted into the casing 52 which in this example is made of a plastic material.

The cutaway section in FIG. 14 reveals a reference fibre 68 positioned adjacent to the sample fibre of the probe 54.

Referring to FIG. 15 the illuminator 56 has a substantially parabolic shaped hollow body 70 with an aperture 72 in which a lamp 74 is positioned. As can be clearly seen more clearly in FIG. 17 the lamp 74 is off centre and spaced from the probe 54 and the reference fibre 68 The body 70 is shaped so that its interior reflective surface 76 illuminates an annulus 78 of light onto an object 90 such as a strawberry. It should be noted that the object may be any plant, biological sample, chemical sample or mineral sample.

The shroud 58 has a rearwall 80 extending to the probe 54 and the fibre 68.

The shroud 58 and the hollow body 70 may be integrally formed as a unit from a suitable solid plastic, e.g. polycarbonate or acrylic. However in this example they are separately formed and the shroud 58 can be detached for replacement. The interior surfaces of the shroud 58 and the body 70 are suitably metalized so that they are highly reflective.

The shroud 58 is shaped so that deflects parts of the light from the lamp 74 and from the reflective surface 76 of the body 70 towards the regions of the annulus 78 This improves the intensity of the annular illumination.

The rear surface of the wall 80 i.e., the entry surface for the NIR illumination, is Fresnel lensed for directing the illumination to the regions of the annular 78. Instead of a Fresnel lens the rear surface may be curved to concentrate the illumination at the regions.

The shroud 58 performs a number of other most useful functions including:

i) It protects the illuminator 56 from the environment and the metal tube sheath of the probe 54 robustly from the intended applications where dropping the gun is probable.

ii) It, at least partially, affords some ambient light shading of the object being measured.

iii) It conveniently separates and or displaces unwanted object or other material, etc, away from the desired area as the gun is pushed toward the sample to be measured.

iv) It allows ready wiping and cleaning with material likely to be on hand, i.e., a shirt tail or handkerchief.

v) It can be made replaceable.

vi) It can be made replaceable for alternative applications, e.g., much larger fruit (watermelons, etc), by unscrewing. In this instance, care has to be taken to ensure proper coupling of the probe 54 and reference fibre 68 ends into the apparatus 50.

FIG. 16 shows an embodiment of the illuminator 56 and the shroud 58 for a larger object 90. As can be seen the detecting end of the probe 54 in this case is substantially flush with the shroud 58.

Figure 19:
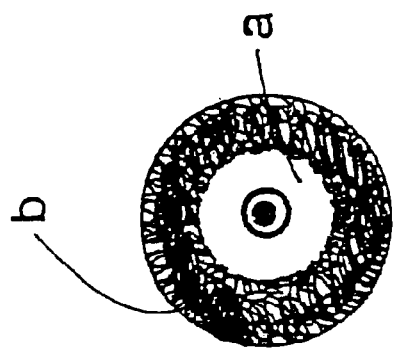
FIG. 19 shows a typical annulus of light produced by the illuminator of the present invention.

The illuminator 56 is arranged to produce an annulus of bright, NIR rich, light surrounding the probe 54 such that the ring of light is as shown in FIG. 19. The region 'b' is the concentrated NIR illumination annulus and 'a' is a region designed not to be (directly) illuminated. This is to maximise, in as much as possible, that light received via the probe 54 which has diffused within the object 90 as shown in FIG. 20.

Figure 20:
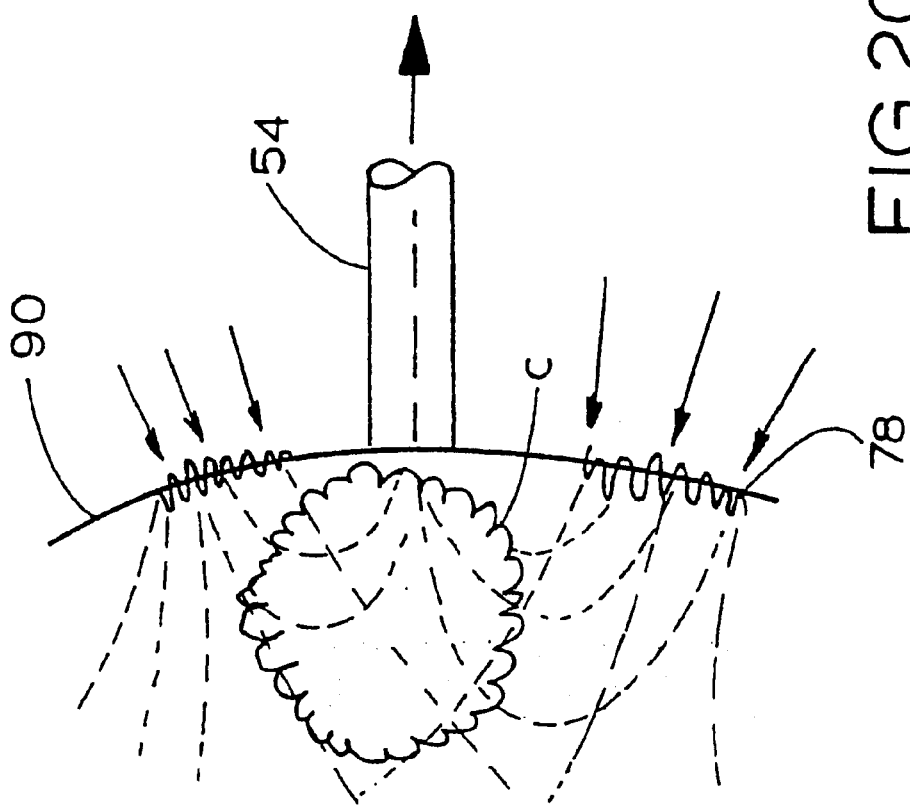
FIG. 20 is a schematic diagram showing illumination of the annular light on the surface of a fruit and a detector disposed to detect scattered light from within the fruit.

As shown in FIG. 20 it is clear that the incident annular illumination 78, which can enter the sampling probe fibre 54, must have (mostly) scattered from the region shown as "c". This minimises noise signals such as light which travels directly along the immediate surface or in the skin of the object or fruit 90 from being detected by the probe 54.

It is also clear from FIG. 20 that the fibre support probe 54, akin to a hypodermic "flanened-end" needle not only provides rigid and maintainable support for the fibre, but also acts as a most effective light shield from ambient and surface scattered light, which would otherwise enter the probe 54 via object or fruit surface irregularities and "cracks and voids".

The reference probe 68 is designed to capture part of the illumination light and minimise any reflected light from the object or fruit 90. Such light, indicative of the spectral characteristic of the illumination is captured by reflection off the shroud's rear surface. This rear surface of the wall 80 is mirrored at a small area or alternatively, roughened slightly to aid its backscatter. In the event the shroud 58 is essentially a solid plastic part, this reference light may be sampled by viewing the back of the illumination lamp, or lamps, by similar fibre, or fibres, capturing means.

The fibre probes 54 and 68, and especially the sample probe 54, are intended to be essentially coincident with an imaginary "gun barrel" axis.

The reflective surface 76 of the illuminator 56 is computer designed to optimally produce the annular illumination 78.

The annular illumination 78 allows light to scatter or diffuse in the object 90 being tested before entering the probe 54. This arrangement prevents bright light immediately around the detector probe 54 and thereby avoiding the disadvantage of having a major proportion of light which travels just a very short distance in the close, thin, skin region of the sample being inspected. NIR spectral properties of this small depth, and indeed small area, of the skin is not a reliable indication of the properties desired to be measured.

Figure 18:
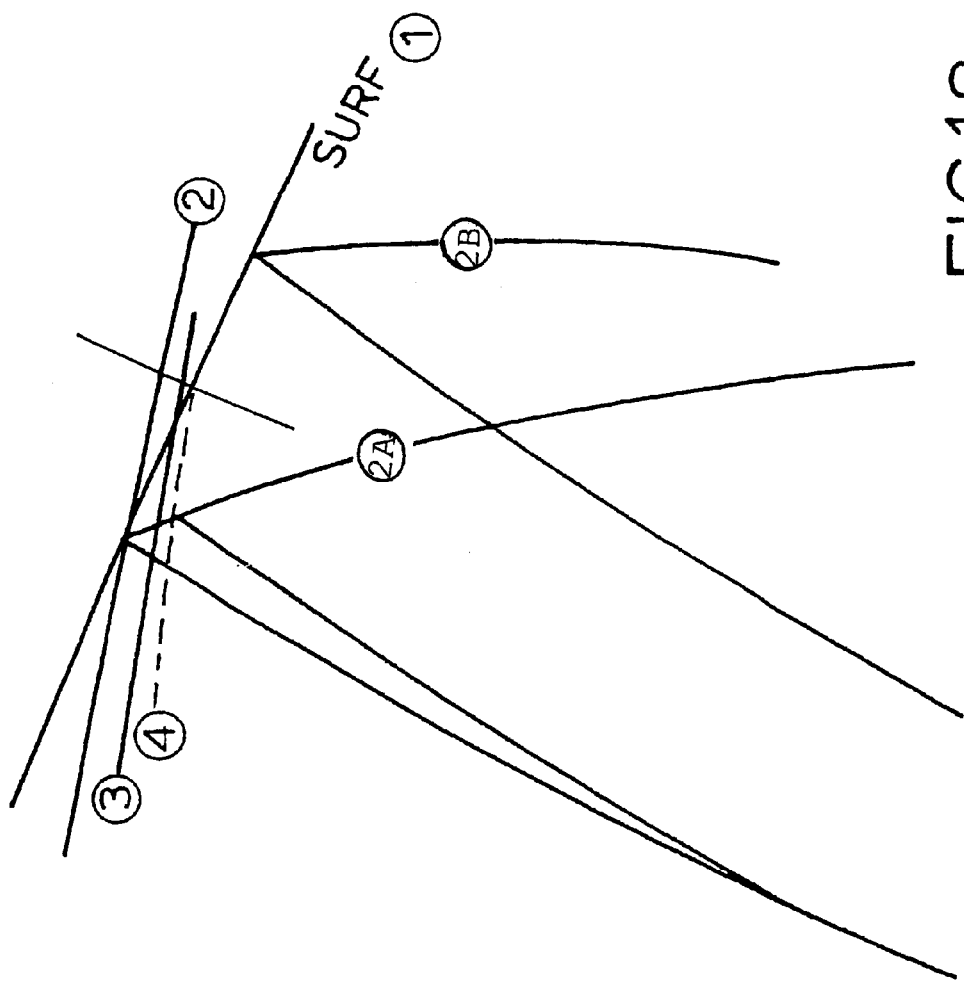
FIG. 18 is a diagram showing the steps in computing the portions forming the reflective surface of the illuminator.

The reflective surface 76 is formed using an optical ray tracing method as shown in FIG. 18. Individual light rays, considered to be emanating from the very small filament of the illumination lamp 74 (which is off center) are directed in small rotational angular displacements toward the rear most portion of the illuminator 56 (immediately adjacent the hole through which the reference and sample fibre probes 54 and 68 pass). By the simple law of reflection, the angle of a very small (essentially rectangular) section 1 of that surface 76, then, can be computed so that for the ray being considered, the reflected part 1A is directed towards the center of the annular ring 78 at the same rotational angle. By stepping emanating rays, one by one, from the lamp(s) through small increments around a half revolution, each ray generates an angled, essentially rectangular shaped, small piece of "flat" reflector directing the rays toward equispaced "dots" around the middle of the annular ring 78. By three dimensional geometry, these reflector facet surfaces schematically shown as 1 to 4 are joined edge to edge.

Once one piece is computed, the program then proceeds to calculate a reflection angle required on that surface to properly direct the adjacent ray 2A. Choosing a new surface 2 at that point with the proper angle, and repeating the above steps for another nearby section 3, it can compute the line of intersection of the two planar elements at their joining edge.

At the completion of a half revolution each way, the two "faceted" reflector rings should join, so checking the calculations.

When one faceted ring of the reflective surface 76 is computed, another, adjacent, faceted ring may be computed similarly such that its inner edges meet the outer edges of the previously computed reflector ring.

And in this manner, a series of "concentric" faceted reflector "rings" can be computed progressing around the axis of the reflective surface in rings, and each ring incrementally stepping away from the fibre probes' hole to the outermost edge at the front of the gun's' reflective surface.

It transpires that these faceted segments can be smoothed to a continuously complex curved surface such that the reflecting angle at the centre of each original facet, and its position, remains the same at points on the new smoothed surface. This forms the basic reflector shape and such design process can accommodate an arbitrary number of lamps, each placed in arbitrary positions.

Whilst the above has been given by way of illustrative example of the present invention many variations and modifications thereto will be apparent to those skilled in the art without departing from the broad ambit and scope of the invention as herein set forth.

What is claimed is:

1. An optical apparatus for non-destructively examining an object, the apparatus comprises a light source including an illuminator having a hollow body with a reflective interior surface, and one or more lamps for emitting light of near infrared radiation (NIR), the one or more lamps being disposed so that at least some portions of the emitted light are reflected from the reflective surface, the reflective surface being configured so that the light reflected therefrom forms an annulus beam directed towards an annular region of the object under examination, an aperture arranged for receiving light reflected from, scattered within or passing through the object and for the light to diverge therefrom, means for collimating light arranged so that the light through the aperture incidents thereat is collimated, means for dispersing the collimated light from the collimating means into wavelength components, and means for providing electrical output signals which are respectively proportional to energy levels in the wavelength components.

2. The apparatus according to claim 1 further comprises means for processing the output signals and thereby providing one or more indication signals for respectively indicating one or more characteristics of the object.

3. The apparatus according to claim 2 wherein an indication means is arranged for receiving the one or more indication signals for indicating the or each said indication signals in a suitable form.

4. The apparatus according to claim 2 wherein the apparatus having an interface means to which a computer can be selectively connected thereto for storing the one or more indication signals and/or for further processing the one or more indication signals.

5. The apparatus according to claim 2 wherein the processing means includes a data correlation device adapted to relate the or each of said indication signals to a characteristic of the object.

6. The apparatus according to claim 5 wherein the data correlation device having a set of correlation data for one type of object or a plurality of sets of correlation data for different types of objects.

7. The apparatus according to claim 2 wherein each said characteristic relates to a constituent of the object, including a carbohydrate, starch or a sugar in the form of sucrose, glucose, or fructose.

8. The apparatus according to claim 2 wherein the or each said characteristic relates to a relative concentration of a constituent of the object, including a carbohydrate, starch or a sugar in the form of a sucrose, glucose, or fructose.

9. The apparatus according to claim 2 wherein each said characteristic relates to a physiological state of the object, including a growth state or maturity state in plant.

10. The apparatus according to claim 2 wherein each said characteristic is a signature of vigour of growth or maturity for picking.

11. The apparatus according to claim 5 wherein the data correlation device is arranged for removably connectable to the apparatus so that the apparatus can be selectively connected to the data correlation device with a set of correlation data for a particular object under examination.

12. The apparatus according to claim 5 wherein the data correlation device is contained in a printed circuit card including a PCMCIA card.

13. The apparatus according to claim 1 wherein the output signal providing means includes an detection arrangement for detecting the wavelength components.

14. The apparatus according to claim 13 wherein the apparatus has a focusing arrangement for focusing the wavelength components onto the detection arrangement and an optical conveying means for conveying the light reflected from or through the object to the aperture, the conveying means including an optical fibre.

15. The apparatus according to claim 1 wherein the aperture is positioned at about the focal length of the collimating means and having one or more parallel slits of a suitable width.

16. The apparatus according to claim 1 wherein the collimating means is a collimating achromatic lens and the dispersing means are one or more prisms of any suitable configuration including equilateral prism(s).

17. The apparatus according to claim 14 wherein the focusing arrangement includes one or more focusing lenses for focusing the wavelength components onto the detection arrangement and the one or more focusing lenses are configured so that a linear dispersion of the spectrum can be provided across the detection arrangement.

18. The apparatus according to claim 13 wherein the detection arrangement includes a plurality of detection elements arranged in a matrix of at least 2×2 (4) detection elements for providing the electrical output signals in response to detection of the wavelength components.

19. The apparatus according to claim 1 wherein the apparatus further including housing means configured for locating therein said light source, said collimating means, said dispersing means and said output signal providing means, whereby the apparatus is arranged in a compact form so that the apparatus can be used on field or in situ.

20. The apparatus according to claim 19 wherein the housing means is arranged so that in use a user can operate the apparatus with one hand, or attach the apparatus on a part of the user body such as on a wrist.

21. The apparatus according to claim 19 wherein the housing means includes a substantially light proof first housing member in which the aperture, the collimating means, the dispersing means and the output signal providing means are located, the first housing member is arranged to reduce or eliminate interference from background radiation and reflections from optical surfaces; and a second housing member in which the light source is located and the second housing member has a gap into which at least part of the object for examination can be inserted, the second housing member being fixedly or removably connected to the first housing member.

22. The apparatus according to claim 1 wherein said hollow body is substantially conical or half egg shell shaped.

23. The apparatus according to claim 1 wherein the annulus beam is arranged around a light detection probe for detecting scattered light from said object.

24. The apparatus according to claim 23 wherein the detection probe is positioned along an axis of the hollow body and the light source is positioned at an angle to said axis.

25. The apparatus according to claim 1 wherein the illuminator is provided with a shroud downstream of the light reflected from said reflective surface.

26. The apparatus according to claim 25 wherein the shroud has a partly or wholly reflective interior surface for redirecting portions of the light from said light source and/or said interior surface of the body to said region of the object.

27. The apparatus according to claim 25 wherein the shroud has a rear wall arranged to direct light towards the region.

28. The apparatus according to claim 25 wherein the shroud is removably fixed so that it can be easily replaced.

29. The apparatus according to claim 23 wherein the detection probe including an optical fibre arranged within a protective probe.

30. The apparatus according to claim 23 wherein a reference probe is arranged substantially parallel to said detection probe.

* * * * *